United States Patent [19]

Hansen et al.

[11] Patent Number: 5,159,105
[45] Date of Patent: Oct. 27, 1992

[54] HIGHER PENTAFLUOROSULFANYL-FLUOROALIPHATIC CARBONYL AND SULFONYL FLUORIDES, AND DERIVATIVES

[75] Inventors: John C. Hansen, Lakeland; Patricia M. Savu, Maplewood, both of Minn.

[73] Assignee: Minnesota Mining and Manufacturing Company, St. Paul, Minn.

[21] Appl. No.: 486,115

[22] Filed: Feb. 28, 1990

[51] Int. Cl.$^5$ .................... C07C 205/00; C07C 53/21
[52] U.S. Cl. ..................... 560/125; 560/147; 560/223; 562/605; 562/825; 562/849; 568/842
[58] Field of Search .............. 560/125, 223, 147; 562/605, 825, 849; 568/842

[56] References Cited

U.S. PATENT DOCUMENTS

| | | | |
|---|---|---|---|
| 2,519,983 | 8/1950 | Simons | 204/62 |
| 2,567,011 | 9/1951 | Diesslin et al. | 260/465.7 |
| 2,666,797 | 1/1954 | Husted et al. | 260/633 |
| 2,691,043 | 10/1954 | Husted et al. | 260/583 |
| 2,732,398 | 1/1956 | Brice et al. | 260/503 |
| 2,759,019 | 8/1956 | Brown et al. | 260/556 |
| 2,764,602 | 9/1956 | Ahlbrecht | 260/404.5 |
| 2,803,656 | 8/1957 | Ahlbrecht et al. | 260/556 |
| 3,028,321 | 4/1962 | Danielson et al. | 204/59 |
| 3,094,547 | 6/1963 | Heine | 260/461 |
| 3,131,217 | 4/1964 | Ray et al. | 260/543 |
| 3,219,690 | 11/1965 | Sheppard | 260/515 |
| 3,250,807 | 5/1966 | Fritz et al. | 260/535 |
| 3,398,182 | 8/1968 | Guenthner et al. | 260/455 |
| 3,448,121 | 6/1969 | Woolf et al. | 260/333 |
| 3,475,453 | 10/1969 | Gilbert et al. | 424/335 |
| 3,562,156 | 2/1971 | Francen | 252/8.05 |
| 3,692,643 | 9/1972 | Holland | 204/59 R |
| 4,024,178 | 5/1977 | Landucci | 260/472 |
| 4,094,911 | 6/1978 | Mitsch et al. | 260/615 |
| 4,359,096 | 11/1982 | Berger | 169/44 |
| 4,484,990 | 11/1984 | Bultman et al. | 204/106 |
| 4,540,497 | 9/1985 | Chang et al. | 252/8.8 |
| 4,606,737 | 8/1986 | Stern | 8/115.6 |
| 4,647,413 | 3/1987 | Savu | 260/544 F |
| 4,668,406 | 5/1987 | Chang | 252/8.75 |
| 4,686,300 | 8/1987 | Krespan | 549/313 |
| 4,739,103 | 4/1988 | Hansen et al. | 560/125 |
| 4,766,248 | 8/1988 | Krespan | 568/31 |
| 4,849,540 | 7/1989 | Sitzmann et al. | 560/156 |

FOREIGN PATENT DOCUMENTS

0062430A1 3/1982 European Pat. Off.

OTHER PUBLICATIONS

3M Company trade bulletin 98-0211-2213-4 (38.3) BPH, issued Mar., 1988.
R. Guenthner and M. L. Vietor, *I&EC Product Research and Development*, 1; No. 3, 165-169 (1961).
M. T. Pike, Paint and Varnish Production, Mar. 1972, pp. 27-32.
H. C. Fielding, "Organofluorine Compounds and Their Applications," R. E. Banks, Ed., Society of Chemical Industry, pp. 215-234 (1979).
R. A. Guenthner, *Kirk Othmer Encyc. of Chem. Tech.*, 3rd Ed., John Wiley & Sons, New York, 10, 897-900, 952-955 (1980).
McGraw-Hill *Encyclopedia of Science & Technology*, 6th Ed., 7, 214-216 (1987).
Ullmann's *Encyclopedia of Industrial Chemistry*, A11, pp. 371-375 (1988).
Lovelace et al., "Aliphatic Fluorine Compounds," Reinhold Publishing Co., N.Y., pp. 335-336 (1958).
Severson et al., "Abstracts of Papers," 128th Meeting, Amer. Chem. Soc. 1955, p. 35M.
Hazeldine and Hyman, *J. Chem. Soc.*, 2684-9 (1956).
Bekker, et al., Chem. Abstr., 74, 99366m (1971).
Clemons et al., *Analytical Chemistry*, 38, No. 1, 133 (1966).
Canich et al., *Inorg. Chem.*, 23, No. 26, 4403 (1984).
Damerius et al., *Angew. Chem., Inc. Ed. Engl.* 28, 769 (1989).
Shepard, *J. Am. Chem. Soc.*, 62, 101 (1962).
Thrasher et al., *Inorg. Chem.* 27, 570 (1988).
Gard et al, *Fluorine Chem.* 1, 487 (1971/72).
Brant et al., *J. Electron Spectrosc. Relat. Phenom.*, 22, 119 (1981).
Canich et al., *Inorg Chem.*, 24, 3668 (1985).
"Fluroine Chemistry", edited by J. H. Simons, Pub. 1950, Academic Press, Inc., New York, pp. 416-418.

*Primary Examiner*—Paul J. Killos
*Attorney, Agent, or Firm*—Gary L. Griswold; Walter N. Kirn; Carolyn V. Peters

[57] ABSTRACT

Pentafluorosulfanyl fluoroaliphatic carbonyl and sulfonyl fluorides, derivatives of the acid fluorides and the preparation and use of the acid fluorides and derivatives. The fluoroaliphatic moiety of said acid fluorides comprise at least three fully-fluorinated carbon atoms. The derivatives of the acid fluorides are useful as surface-active agents and surface-treating agents.

27 Claims, No Drawings

HIGHER PENTAFLUOROSULFANYL-FLUOROALIPHATIC CARBONYL AND SULFONYL FLUORIDES, AND DERIVATIVES

This invention relates to pentafluorosulfanyl-fluoroaliphatic carbonyl and sulfonyl fluorides, derivatives of such acid fluorides, and the preparation and use of such acid fluorides and derivatives. In another aspect it relates to the use of surface-active agents to modify the surface and interfacial tensions of liquids. In another aspect it relates to the use of surface-treating agents to modify surface properties of textiles and other substrates, for example, to impart oil and water repellancy thereto.

Fluorocarbon derivatives (sometimes called organofluorine compounds or fluorochemicals) are a class of substances containing portions which are fluorocarbon in nature, e.g. hydrophobic, oleophobic, and chemically inert, and portions which are organic or hydrocarbon in nature, e.g. chemically reactive in organic reactions. The class includes some substances which are familiar to the general public, such as those which give oil and water repellancy and stain and soil resistance to textiles, e.g. Scotchgard ™ carpet protector. Other substances of the class have various industrial uses, such as reducing the surface tension of liquids, reducing evaporation and flammability of volatile organic liquids, and improving the leveling of organic polymer coatings. Examples of industrial substances are the Fluorad ™ fluorochemical surfactants described in 3M Company trade bulletin 98-0211-2213-4 (38.3) BPH, issued March, 1988.

An industrial method of producing many organofluorine compounds or their precursors is the fluorination process, commercialized initially in the 1950s by 3M Company, which comprises passing an electric current through a mixture of the organic starting compound and liquid anhydrous hydrogen fluoride. This fluorination process is commonly referred to as the "Simons electrochemical fluorination process" or simply the "Simons process" and the electrolytic cell used therein is commonly referred to as the "Simons cell". Some early patents describing such technology are U.S. Pat. Nos. 2,519,983 (Simons), 2,567,011 (Diesslin et al.), 2,666,797 (Husted et al.), 2,691,043 (Husted et al.), and 2,732,398 (Brice et al.); they describe the preparation of such organofluorine compounds as fluorocarbon carbonyl fluorides, e.g. $CF_3(CF_2)_2COF$, and fluorocarbon sulfonyl fluorides, e.g. $CF_3SO_2F$, and derivatives thereof.

Review articles describing fluorinated carboxylic and sulfonic acids and derivatives, and applications thereof, are:
1. R. A. Guenthner and M. L. Vietor, *I & E C Product Research and Development*, 1, No. 3, 165-169 (1961);
2. M. T. Pike, *Paint and Varnish Production*, March 1972, p. 27-32;
3. H. C. Fielding, *"Organofluorine Compounds and Their Applications,"* R. E. Banks, Ed., Society of Chemical Industry, p. 215-234 (1979);
4. R. A. Guenthner, *Kirk-Othmer Encyclopedia of Chemical Technology*, 3rd Ed., John Wiley & Sons, New York, 10, 897-900, 952-955 (1980);
5. McGraw-Hill *Encyclopedia of Science & Technology*, 6th Edition, 7, 214-216 (1987)); and
6. *Ullmann's Encyclopedia of Industrial Chemistry*, A11, p. 371-375 (1988).

The utility of organofluorine compounds as surface-active agents (or surfactants) and surface-treating agents is due in large part to the extremely low free-surface energy of a $C_6$-$C_{12}$ fluorocarbon group, according to Fielding, supra, at p. 214. At pages 215-216 of his review, Fielding states that a polyacrylate with a perfluoroalkyl side chain, —$C_7F_{15}$, has the lowest critical surface tension and hence is the most difficult to wet. In considering the surface tension of an aqueous system, Fielding goes on to say, perfluoroalkyl groups packed at the air-water interface should provide the lowest free-energy surface and give the greatest lowering of surface tension.

Generally, the organofluorine substances described above are those which have carbon-bonded fluorine in the form of a monovalent fluoroaliphatic radical such as a perfluoroalkyl group, typically $C_nF_{2n+1}$, where n is at least 3, the terminal part of which group is trifluoromethyl, —$CF_3$.

There are some known organofluorine compounds having an organic portion and sulfur-bonded fluorine in the form of a pentafluorosulfanyl group $F_5S$ (sometimes called pentafluorothio or sulfur pentafluoride and alternatively depicted as $SF_5$) bonded to an aliphatic or aromatic moiety, e.g. $F_5S$—$CH_2COCl$, $F_5S$—$CH_2CH_2OH$, $F_5S$—$CH_2CH_2OC(OR)_3$ (where R is an $NO_2$-containing alkyl), $F_5S$—$CH(Br)COOH$, and $F_5S$—$R(X)_n$ (where R is aromatic, X is halogen, and n is 0 to 5), e.g. see U.S. Pat. Nos. 3,219,690 (Sheppard et al.) and U.S. Pat. No. 4,849,540 (Sitzmann et al.). (There are also some fluorocarbon pentafluorosulfides, e.g. $F_5S$—$CF_3$, $F_5S$—$C_2F_5$, and $F_5S$—$C_4F_9$, made by electrochemical fluorination; see Lovelace et al., "Aliphatic Fluorine Compounds," Reinhold Publishing Co., New York, p. 335-336 (1958).) But there are only a small number of known organofluorine compounds having a fluorocarbon or saturated fluoroaliphatic portion which terminates in a pentafluorosulfanyl group. Specifically, Severson et al., in "Abstracts of Papers," 128th Meeting, American Chemical Society, 1955, p. 35M, discloses the lower pentafluorosulfanyl-fluoroaliphatic carbonyl fluoride $F_5S(CF_2)_2COF$, prepared by electrochemical fluorination of an unnamed reactant. The simplest pentafluorosulfanyl-fluoroaliphatic acid fluoride, $F_5S$—$CF_2$—$COF$, was reportedly obtained impure and in low yield by the electrolysis of HS—$CH_2$—COOH in anhydrous hydrofluoric acid: see Hazeldine and Nyman, *J. Chem. Soc.*, 2684-9 (1956). The corresponding carboxylic acid made by radical addition of fluorinated precursor and the silver salt, as well as the methyl and ethyl esters thereof, have also been described; see Bekker, et al., *Chem. Abstr.*, 74, 9366m (1971). Telomers of the formula $F_5S(CF_2)_nCl$, where n is 2, 4, or 6, are disclosed, for example, by Clemons et al. in *Analytical Chemistry*, 38, No. 1, 133 (1966). Perhalogenated iodides containing a sulfur pentafluoride group, such as iodotetrafluoroethylsulfurpentafluoride and iodoperfluoropropylsulfurpentafluoride, are disclosed in Brit. Pat. Specification 1,167,112 (Allied Chem. Corp.) as useful as fumigants, effective against insects, and as intermediates for compounds for preparation of coatings which are resistant to water, oil, and stains. Unsaturated compounds containing $F_5S$, such as $F_5S$—CF=$CF_2$ and $F_5S(CF_2)_2CF$=$CF_2$, are disclosed in U.S. Pat. No. 3,131,217 (Ray et al.), U.S. Pat. No. 3,448,121 (Woolf et al.), and Brit. Pat. Specification 1,145,263 as useful as a monomer or in making oxetanes useful as heat transfer media, and in U.S. Pat. No. 3,475,453 (Gilbert et al.) as a fumigant. Said unsaturated compound $F_5S—CF=CF_2$ can be reacted with $SO_3$ to make

$F_5S—CFCF_2OSO_2$, which can be converted to $F_5S—CFH—SO_2F$, according to Canich et al., *Inorg. Chem.*, 23, No. 26, 4403 (1984). Damerius et al., disclose $F_5S—C(CF_3)=SF_2$ in *Angew. Chem., Inc. Ed. Engl.* 28, 769 (1989).

The $F_5S$ group is said to have been found to be more electron-withdrawing than the $CF_3$ group; see Shepard, *J. Am. Chem. Soc.*, 62, 101 (1962). Thrasher et al. in *Inorg. Chem.*, 27, 570 (1988) describe the effect on the electronegativity of amino groups, $R_2N—$, upon changing R from $CF_3$ to $F_5S$. However, Gard et al. in *Fluorine Chem.* 1, 487 (1971/72), Brant et al. in *J. Electron Spectrosc. Relat Phenom.*, 22, 119 (1981), and Canich et al. in *Inorg. Chem.* 24, 3668 (1985) state that the electron-withdrawing effect of the $CF_3$ group is greater than the $F_5S$ group.

Briefly, the present invention, in one aspect, provides new fluorochemical compositions of matter which comprise one or a mixture of higher, pentafluorosulfanyl, saturated fluoroaliphatic carbonyl fluorides or sulfonyl fluorides. The fluoroaliphatic moiety or radical comprises at least three fully-fluorinated, saturated aliphatic carbon atoms, which are preferably in a chain that can be a straight (or normal) chain or branched chain, e.g., $—(CF_2)_3—$ and $—CF(CF_3)CF_2—$, or a cyclic or part of a cyclic chain, one of said three carbon atoms preferably being bonded to the hexavalent sulfur atom of the $F_5S$ moiety, the acid halide moiety in the substance being preferably bonded to a different carbon atom of the fluoroaliphatic moiety. In a further aspect, the invention provides pentafluorosulfanyl-fluoroaliphatic derivatives of said acid fluorides, such as those derivatives with functional organic or inorganic oxygen-containing groups, e.g. $F_5S(CF_2)_4CO_2H$ and $F_5S(CF_2)_4SO_3Li$.

(For purposes of brevity, the above-described classes of acid fluorides and derivatives are generically referred to herein on occasion as the fluorochemicals or fluorochemical compositions of this invention, and the term acid fluoride(s) is used as a generic term to mean said carbonyl fluoride(s) and said sulfonyl fluoride(s).)

The pentafluorosulfanyl-fluoroaliphatic moiety is hydrophobic and oleophobic, thermally stable, and inert or unreactive. Fluorochemicals of this invention have been found to have good thermally stability and exhibit surface-active properties which make them useful as surface-active agents (or surfactants) in modifying the surface and interfacial tensions of liquids and others are useful as surface-treating agents (e.g. in the form of coatings) in modifying the surface properties of substrates such as the fibrous substrates of textiles, leather, and paper, e.g. in modifying the oil and water repellancy of the substrates as indicated by the contact angle of a drop of a liquid, such as mineral oil, on such substrates. Surprisingly, fluorochemicals of this invention have some surface-active properties equivalent to or superior to those of trifluoromethyl-terminated fluorochemicals and have utility in the same applications.

The fluorochemical compositions of this invention comprise, consist essentially of, or consist of one or more of said higher, pentafluorosulfanyl, saturated fluoroaliphatic acid fluoride compounds or derivatives thereof. Those compositions can contain a predominant amount of said acid fluorides or derivatives thereof, for example, at least 20 weight percent (but such composition can be diluted or mixed with other materials, e.g. solvents, for purposes of application or use). Some of the fluorochemical compositions will be normally liquid and others will be normally solid. The compositions will typically comprise polydisperse mixtures of straight and branched chain compounds and the molecules in such compositions will generally include those of the same type but vary in the chain length or in the number of carbon atoms in the fluoroaliphatic portion or vary in some other structural detail. For example, a fluorochemical of this invention comprises a mixture of $F_5S—CF(CF_3)CF_2CO_2CH_3$, $F_5S—CF_2CF(CF_3)CO_2CH_3$, and $F_5S—(CF_2)_3CO_2CH_3$. The distillation or purification of the compositions as made generally will result in a range of different molecular species in the compositions. Some of these mixtures may be somewhat difficult to separate into essentially pure or discreet molecular species. In many if not most applications or uses of the such mixtures, there will be no need to separate them into individual, chemically homogeneous, species in order to achieve desired results, e.g. lowering the surface or interfacial tension of liquids.

Acid fluorides of the fluorochemical compositions of or used in the practice of this invention can be represented by the generic formula $F_5S—R_f—X$, where X is $—COF$ or $—SO_2F$, and by the subgeneric formulas $F_5S—R_f—COF$ and $F_5S—R_f—SO_2F$. $R_f$ is a saturated fluoroaliphatic radical having a chain of at least three fully-fluorinated, saturated aliphatic carbon atoms, one of which is covalently bonded to the sulfur atom of the $F_5S$ group, the acid fluoride moiety being preferably covalently bonded to a different carbon atom of the fluoroaliphatic moiety, and the chain having as many as 20 or more carbon atoms, all or predominantly all of which are fully fluorinated (i.e., all carbon-bonded hydrogen atoms being replaced by fluorine). The skeletal chain of $R_f$ can be straight, branched, or, if sufficiently large, cyclic or contain a cyclic structure, and can be composed of only carbon, hydrogen, and fluorine, or just carbon and fluorine (i.e., $R_f$ can be fully fluorinated or perfluorinated), and it can include catenary divalent oxygen, $—O—$, fluorinated hexavalent sulfur, $—SF_4—$, or trivalent nitrogen,

bonded only to carbon atoms, such hetero atoms being chemically stable linkages between fluorocarbon portions of the fluoroaliphatic radical. The fluoroaliphatic moiety will not contain more than one of said hetero atoms for every two catenary carbon atoms. A preferred embodiment of $R_f$ is a perfluoroalkylene radical of the formula $—C_nF_{2n}—$ where n is at least 3 and can be as high as 20 carbon atoms or more but generally only up to about 6 to 12 carbon atoms since larger radicals represent a less efficient utilization of fluorine than smaller radicals. Another embodiment of $R_f$ is a perfluorinated, saturated cycloaliphatic moiety such as one having 4, 5, or 6 ring carbon atoms, e.g. a perfluorocyclohexylene, $—C_6F_{10}—$, a ring carbon atom of which is covalently bonded to the sulfur atom of the $F_5S$ moiety. Preferably, $R_f$ in the formulas has 4 to 12 carbon atoms.

Examples of $R_f$ are $-(CF_2)_3-$, $-CF(CF_3)CF_2-$, $-(CF_2)_2CF(CF_3)-$, $-(CF_2)_4-$, and $-(CF_2)_8$, and $-(CF_2)_2-O-(CF_2)_3-$.

The acid fluoride compositions of this invention can be prepared by electrochemical fluorination of thio-, dithio-, thiol- (or mercapto-) and hydrogen-containing, saturated or unsaturated, non-fluorinated or partially-fluorinated, non-chlorinated or partially-chlorinated carbonyl or sulfonyl precursors which are fluorinatable, that is, precursors which contain a carbon-bonded sulfur atom and contain carbon-bonded hydrogen atoms which are replaceable with fluorine and the precursors can contain carbon-carbon unsaturation that is saturatable with fluorine. Representative examples of such precursors are thiophenecarbonyl chloride, thiobutyrolactone, mercaptobenzoic acid, 2-thiophenecarboxylic acid, 2-thiophenecarboxaldehyde, 3-methyl-2-thiophenecarbonyl chloride, dithiodihexanoyl chloride, 2,2'-dithiosalicylic acid, 9-mercapto-7-methyl-nonanoic acid, and 11-mercaptoundecanoic acid. Such precursors are relatively unreactive with but soluble in liquid hydrogen fluoride.

The carbonyl fluoride and sulfonyl fluoride fluorochemical compositions of this invention are prepared in good yields as electrochemical fluorination products by the Simons process, viz., by electrolyzing a liquid anhydrous hydrogen fluoride solution of the afore-described sulfur- and hydrogen-containing organic precursor. The electrochemical step is highly energetic and is often accompanied by carbon-carbon bond cleavage that leads to fragmentation and recombination phenomena and results, in general, in a fluorochemical product comprising the aforedescribed mixture of pentafluorosulfanyl acid fluoride compounds, some of which may represent cleavage and/or rearrangement of the carbon skeleton of their precursor, and low and high molecular weight fluorinated by-products, including non-functional pentafluorosulfides, as illustrated in the Examples hereinafter set forth. The fluorochemical product which is relatively insoluble in liquid hydrogen fluoride and can be separated from residual hydrogen fluoride, e.g. by treatment with sodium fluoride, and purified, e.g. by distillation. The fact that a fluorochemical composition of this invention includes a mixture of acid fluoride compounds generally is not detrimental to its utility. In the event it is desired to separate such mixtures into components, the components can be isolated by such conventional separation techniques as distillation, extraction, recrystallization, and chromatography.

The electrochemical fluorination process, that is, the Simons process, used in the preparation of the pentafluorosulfanyl-fluoroaliphatic acid fluoride compositions of this invention, typically involves an electrolytic cell ("Simons cell") in which is suspended an electrode pack comprising series of alternating and closely-spaced iron cathode plates and nickel anode plates. The cell body, made of carbon steel, usually is provided with a cooling jacket, a valved-outlet pipe at the bottom through which can be drained the settled liquid cell-product ("drainings"), a valved inlet pipe at the top of the cell for charging the cell with liquid anhydrous hydrogen fluoride, the fluorinatable organic starting material, and conductivity additive, and an outlet pipe at the top of the cell for removing gaseous cell products evolved in operation of the cell. The outlet pipe can be connected to a refrigerated condenser for condensing hydrogen fluoride vapors which can be drained back into the cell. Said U.S. Pat. No. 2,519,983 contains a drawing of such a Simons electrolytic cell and its appurtenances, and a description and photographs of laboratory and pilot plant cells appear at pages 416–418 of the book "Fluorine Chemistry", edited by J. H. Simons, published in 1950 by Academic Press, Inc., New York.

The Simons cell can be operated at average applied D.C. cell voltages in the range of 4 to 8 volts (sufficiently high but not so high as to generate free fluorine), current density of 4 to 20 mAmp/cm$^2$ of active anode surface, at substantially atmospheric or ambient pressure or higher, and at temperatures ranging from below about 0° C. to about 20° C. or as high as 50° C. (so long as the electrolytic solution remains liquid). The organic starting material or precursor to be fluorinated may be initially present in the electrolytic solution of hydrogen fluoride in an amount of 5 to 20 weight percent, for example. Both the organic starting material and the hydrogen fluoride electrolyte can be replenished from time to time. The conductivity of the electrolytic solution can be increased by adding a conventional carrier electrolyte (conductivity additive), such as sodium fluoride, acetic anhydride, or organic sulfur-containing additive such as that described in U.S. Pat. Nos. 3,028,321 (Danielson), 3,692,643 (Holland), and 4,739,103 (Hansen). The amount of said additive can be, for example, 1 to 20 weight percent by weight of the organic starting material.

Other details of the Simons electrochemical fluorination process and Simons cell will be omitted in the interest of brevity, and the disclosures of such technology in the above-cited patents and text of Simons can be referred to for such detail, which disclosures are incorporated herein by reference.

The carbonyl fluorides and sulfonyl fluorides of this invention are reactive chemicals and can be converted into their reactive or functional derivatives. A class of such derivatives can be represented by the formula $F_5S-R_f-Z$ where $R_f$ is as defined and described above and Z is an organic moiety or an oxygen-containing inorganic moiety that is a one-step or multi-step derivative of $-COF$ or $-SO_2F$. Various functional embodiments of Z, like the precursor acid fluoride moiety, make the derivatives useful reagents for the introduction of the $F_5S-R_f$ moiety into molecules. Z can be an organic functional moiety, i.e., one which contains one or more carbon atoms, such as carbonyl-containing, sulfonyl-containing, alkylene-containing, nitrogen-containing, and oxygen-containing moieties or Z can be an oxygen-containing inorganic moiety, such as sulfonyl-containing and sulfonyloxy-containing moieties. Representative functional Z moieties are, for example, polymerizable groups which will undergo electrophilic, nucleophilic, or free radical reaction, derivatives with such groups being useful to form polymers comprising polymeric chains having a plurality of pendant pentafluorosulfanyl, saturated fluorinated groups each having at least three fully-fluorinated carbon atoms, such pendant groups being bonded to the polymer chain or polymer backbone by, for example, an alkyleneoxycarbonyl or sulfonamidoalkleneoxycarbonyl group through the carbonyl moiety thereof. Derivatives of this invention include carboxylic and sulfonic acids and their metal and ammonium salts, esters, including alkyl and alkenyl esters, amides, dihydroalcohols ($-CH_2OH$), esters of dihydro-alcohols, acrylates (and polyacrylates), mercaptans, alkenyl ethers, etc.. Stated otherwise, Z in the above formulas can be or contain —COOH, —COOM$_{1/v}$, —COONH$_4$, —(CH$_2$)$_n$COOR, —CONH$_2$, —COONR$^1$R$^2$, —CONR$^1$R$^3$A, —(CH$_2$)$_n$OH, —(CH$_2$)$_n$—O—CH$_2$CH—CH$_2$ (with epoxide O)   5

—CHO, —(CH$_2$)$_n$OR, —CF$_2$OCF(CF$_3$)COF, —(CH$_2$)$_n$NCO, —(CH$_2$)$_n$SH, —CN, —SO$_3$H, —SO$_3$M$_{1/v}$, —SO$_3$NH$_4$, —SO$_2$NR$^1$R$^2$, —SO$_2$NR$^1$R$^3$A, —SO$_2$NH$_2$, —SO$_3$R, —(CH$_2$)$_n$I, —(CH$_2$)$_n$SH, —(CH$_2$)NR$^1$R$^2$, —(CH$_2$)OCOCR$^4$=CH$_2$, —CH$_2$OCOCF$_2$SF$_5$, and the like, where M is a metal atom having a valence "v", such as a monovalent metal atom like K or Na; R is alkyl (e.g. with 1 to 14 carbon atoms), aryl (e.g. with 6 to 10 or 12 ring carbon atoms), or a combination thereof (e.g. alkaryl or aralkyl); R$^1$ and R$^2$ are each independently H or R; R$^3$ is alkylene (e.g. with 1 to 13 carbon atoms; R$^4$ is H or CH$_3$; A is an aliphatic or aromatic moiety, which can contain a carboxy or sulfo group or an alkali metal or ammonium salt or ester thereof, a carboxamido, a sulfonamido, or contain 1 to 3 hydroxy groups, 1 or more ether-oxygen or oxirane oxygen atoms, a cyano group, a phosphono group, or one or more primary, secondary, or tertiary amine groups, or quaternized amine group, or other functional group.

Acid fluorides of this invention can be prepared electrochemically by the Simons process by the following general illustrative process schemes 1a, 1b, etc., which utilize aliphatic or aromatic mercapto-acids, disulfides, thiolactones, or thiophene acids as the starting materials.

HS—R—COOH + HF ⟶ F$_5$S—R$_f$—COF    1a

HS—R—SO$_3$H + HF ⟶ F$_5$S—R$_f$—SO$_2$F    1b

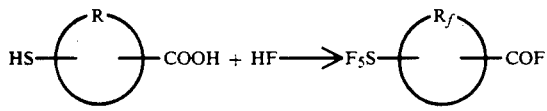    2a

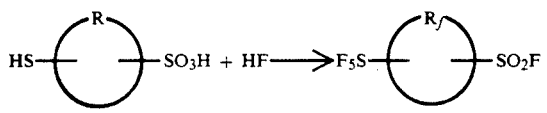    2b

ClOC—R—S—S—R—COCl + HF ⟶ F$_5$S—R$_f$—COF    3a

ClO$_2$S—R—S—S—R—SO$_2$Cl + HF ⟶ F$_5$S—R$_f$—SO$_2$F    3b

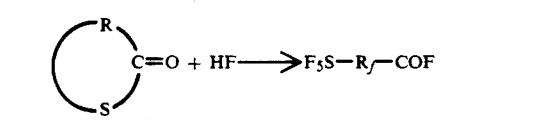    4a

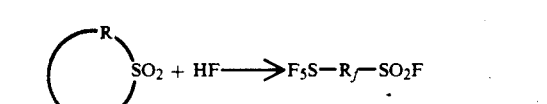    4b

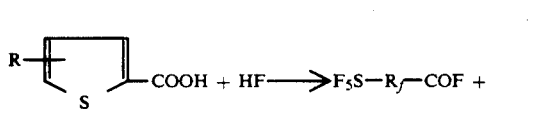    5a

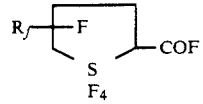

-continued

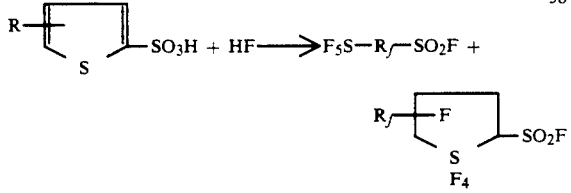    5b

The rings in schemes 2a, 2b represent cycloaliphatic structures, those of the fluorinated products being saturated. The rings in schemes 4a, 4b represent sulfur heterocycles. The sulfur heterocyclic structures in the products of schemes 5a and 5b are saturated, and they are also perfluorinated as symbolizing by the "F" within their rings.

Examples of mercapto-acid starting materials which may be used in schemes 1a and 1b include 4-mercaptobutyric acid or its sulfonic acid counterpart. Aromatic mercapto-acids, such as 2-mercaptobenzoic or 2-mercaptobenzenesulfonic acid, can also be employed, as shown in schemes 2a and 2b. Disulfides which can be reacted according to schemes 3a and 3b above include dithiohexanoyl chloride. Schemes 4a and 4b utilize a thiolactone or thiosultone as a starting material, a specific example being thiobutyrolactone. Variously substituted thiophenes, such as 2-thiophenecarbonyl chloride or 2-thiophenesulfonyl chloride, and alkylthiophene acid chlorides, such as 3-methylthiophenecarbonyl chloride, 5-methylthiophenecarbonyl chloride, and sulfonyl counterparts, when subjected to electrochemical fluorination, produce the linear and cyclic perfluorothiolane compounds shown in schemes 5a and 5b above as the predominant products.

The acid fluorides, F$_5$S—R$_f$—COF and F$_5$S—R$_f$—SO$_2$F, can be used, as illustrated in the following derivative schemes 6a, 6b, etc., to prepare derivatives within the scope of this invention.

F$_5$S—R$_f$—COF + H$_2$O → F$_5$S—R$_f$—COOH    6a

F$_5$S—R$_f$—SO$_2$F + M$_{1/v}$OH → F$_5$S—R$_f$—SO$_3$M$_{1/v}$
F$_5$S—R$_f$—SO$_3$M + H$^+$ + H$_2$O → F$_5$S—R$_f$—SO$_3$H    6b

F$_5$S—R$_f$—COF + M$_{1/v}$OH → F$_5$S—R$_f$—CO$_2$M$_{1/v}$    7a

F$_5$S—R$_f$—SO$_2$F + M$_{1/v}$OH → F$_5$S—R$_f$—SO$_3$M$_{1/v}$    7b

F$_5$S—R$_f$—COF + NH$_4$OH → F$_5$S—R$_f$—CO$_2$NH$_4$    8a

F$_5$S—R$_f$—SO$_2$F + NH$_4$OH → F$_5$S—R$_f$—SO$_3$NH$_4$    8b

F$_5$S—R$_f$—COF + ROH BF$_3$ → F$_4$S—R$_f$—CO$_2$R    9a

F$_5$S—R$_f$—SO$_2$F + N(C$_5$H$_5$)$_3$ + ROH → F$_5$S—R$_f$—SO$_3$R    9b

F$_5$S—R$_f$—CO$_2$R + NaBH$_4$ → F$_5$S—R$_f$—CH$_2$OH    10a

F$_5$S—R$_f$—SO$_2$F + NHR$^1$(CH$_2$)$_n$OH → F$_5$S—R$_f$—SO$_2$NR$^1$(CH$_2$)$_n$OH    10b

F$_5$S—R$_f$—CH$_2$OH + RCOOH → F$_5$S—R$_f$—CH$_2$OCOR    11a

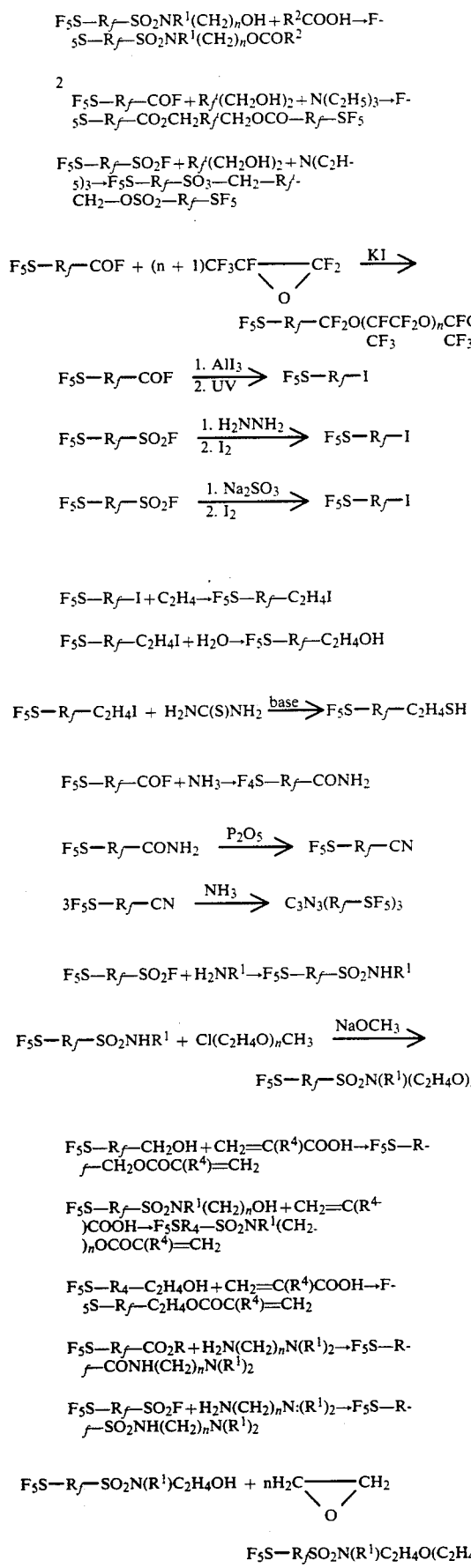
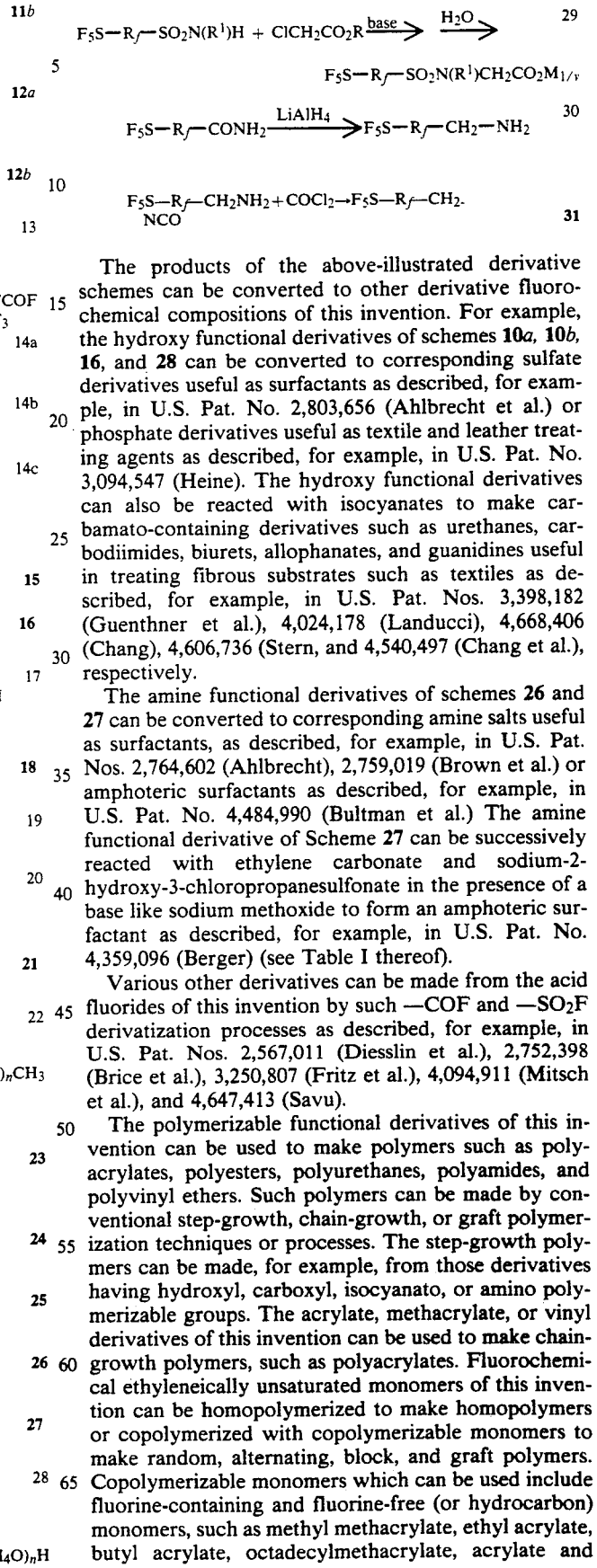

The products of the above-illustrated derivative schemes can be converted to other derivative fluorochemical compositions of this invention. For example, the hydroxy functional derivatives of schemes 10a, 10b, 16, and 28 can be converted to corresponding sulfate derivatives useful as surfactants as described, for example, in U.S. Pat. No. 2,803,656 (Ahlbrecht et al.) or phosphate derivatives useful as textile and leather treating agents as described, for example, in U.S. Pat. No. 3,094,547 (Heine). The hydroxy functional derivatives can also be reacted with isocyanates to make carbamato-containing derivatives such as urethanes, carbodiimides, biurets, allophanates, and guanidines useful in treating fibrous substrates such as textiles as described, for example, in U.S. Pat. Nos. 3,398,182 (Guenthner et al.), 4,024,178 (Landucci), 4,668,406 (Chang), 4,606,736 (Stern, and 4,540,497 (Chang et al.), respectively.

The amine functional derivatives of schemes 26 and 27 can be converted to corresponding amine salts useful as surfactants, as described, for example, in U.S. Pat. Nos. 2,764,602 (Ahlbrecht), 2,759,019 (Brown et al.) or amphoteric surfactants as described, for example, in U.S. Pat. No. 4,484,990 (Bultman et al.) The amine functional derivative of Scheme 27 can be successively reacted with ethylene carbonate and sodium-2-hydroxy-3-chloropropanesulfonate in the presence of a base like sodium methoxide to form an amphoteric surfactant as described, for example, in U.S. Pat. No. 4,359,096 (Berger) (see Table I thereof).

Various other derivatives can be made from the acid fluorides of this invention by such —COF and —SO$_2$F derivatization processes as described, for example, in U.S. Pat. Nos. 2,567,011 (Diesslin et al.), 2,752,398 (Brice et al.), 3,250,807 (Fritz et al.), 4,094,911 (Mitsch et al.), and 4,647,413 (Savu).

The polymerizable functional derivatives of this invention can be used to make polymers such as polyacrylates, polyesters, polyurethanes, polyamides, and polyvinyl ethers. Such polymers can be made by conventional step-growth, chain-growth, or graft polymerization techniques or processes. The step-growth polymers can be made, for example, from those derivatives having hydroxyl, carboxyl, isocyanato, or amino polymerizable groups. The acrylate, methacrylate, or vinyl derivatives of this invention can be used to make chain-growth polymers, such as polyacrylates. Fluorochemical ethyleneically unsaturated monomers of this invention can be homopolymerized to make homopolymers or copolymerized with copolymerizable monomers to make random, alternating, block, and graft polymers. Copolymerizable monomers which can be used include fluorine-containing and fluorine-free (or hydrocarbon) monomers, such as methyl methacrylate, ethyl acrylate, butyl acrylate, octadecylmethacrylate, acrylate and methacrylate esters of poly(oxyalkylene) polyol oligomers and polymers, e.g., poly(oxyethylene) glycol dimethacrylate, glycidyl methacrylate, ethylene, vinyl acetate, vinyl chloride, vinylidene chloride, vinylidene fluoride, acrylonitrile, vinyl chloroacetate, isoprene, chloroprene, styrene, butadiene, vinylpyridine, vinyl alkyl ethers, vinyl alkyl ketones, acrylic and methacrylic acid, 2-hydroxyethyl acrylate, N-methylolacrylamide, 2-(N,N,N-trimethylammonium)ethyl methacrylate and the like.

The polymers can be applied in the form of an aqueous or non-aqueous solution or emulsion as a coating or finish to modify the free surface energy of a substrate, e.g. a non-porous substrate such as glass, metal, plastic, and ceramic or a fibrous or porous substrate such as textile, e.g., nylon carpet fiber or polyester outerwear fabrics, leather, paper, paperboard, and wood to impart oil and water repellency thereto, as described, for example, in the Banks reference supra.

The relative amounts of various comonomers which can be used with the pentafluorosulfanyl monomer of this invention generally will be selected empirically and will depend on the substrate to be treated, the properties desired from the fluorochemical treatment, e.g., the degree of oil and/or water repellency desired, and the mode of application to the substrate. Generally, in the case of copolymers, of the interpolymerized or repeating units in the polymer chain, 5 to 95 mole percent of such units will contain pendant pentafluorosulfanylfluoroaliphatic groups. The pentafluorosulfanyl-fluoroaliphatic polymers of this invention can be blended with other or known polymers, such as perfluoromethylterminated fluoroaliphatic vinyl polymers, and the blend used to modify surface properties, e.g. of textiles such as fabrics to provide them with improved properties such as oil and water repellancy.

Fluorochemicals of this invention which are useful as surfactants generally are those having a polar group bonded to the fluoroaliphatic moiety, $R_f$, such as $-CO_2Na$, $-SO_2NHC_3H_6N^+(CH_3)_3Cl^-$, $-SO_2N(C_2H_5)C_2H_4O(C_2H_4O)_7H$, and $-CONHC_3H_6N^+(CH_3)_2CH_2CO_2^-$, these moieties being representative of the polar groups in anionic, cationic, non-ionic, and amphoteric surfactants, respectively. The surfactants are useful in improving or imparting properties to aqueous and non-aqueous (organic) liquid systems such as wetting, penetration, spreading, leveling, foaming, foam stabilization, flow properties, emulsification, dispersability, and oil, water, and soil repellency. Said liquid system generally will comprise a liquid phase (in which the surfactant will be dissolved or dispersed) and one or more other phases selected from the group consisting of another liquid phase, a gas phase, and a phase of dispersed solids (e.g. polymer solids), and the system can be in the form of an emulsion, suspension, or foam (such as an air foam). Examples of such liquid systems, or application areas for said surfactants, include rinsing, cleaning, etching, and plating baths, floor polish emulsions, photographic processes, water base coatings, solvent based coatings, alkaline cleaners, fluoropolymer emulsions, soldering systems, and specialty inks, such as described, for example, in said 3M Bulletin 98-0211-2213-4 (38.3) BPH.

The fluorochemicals useful as surfactants also can be incorporated into or mixed with other substances. For example, if sufficiently thermally stable, they can be incorporated into polymeric materials, such as polyamides, e.g. nylon, or polyolefins, e.g. polypropylene, which are cast, blown, extruded, or otherwise formed into shaped articles, such as films and fibers, the so-incorporated fluorochemicals modifying the properties of the shaped articles, such as the oil and water repellancy of their surfaces. The fluorochemical surfactants of this invention can also be mixed with other surfactants, such as hydrocarbon surfactants and/or the conventional fluorochemical surfactants, e.g. those disclosed in said U.S. Pat. Nos. 2,567,011 and 2,732,398, which have fluoroaliphatic radicals that terminate with perfluoromethyl instead of pentafluorosulfanyl, and such mixed surfactants used to form, for example, aqueous, film-forming foams as described in U.S. Pat. No. 3,562,156 (Francen).

Objects and advantages of this invention and the preparation and properties of specific compounds and compositions within the scope of this invention are illustrated in the Examples below. In these examples, "GC" means gas chromatograph, "FTIR" means Fourier transform infrared, "MS" means mass spectroscopy, "nmr" means nuclear magnetic resonance, and "IR" means infra red. The $F^{19}$ nmr analyses were obtained in $CFCl_3$ on a 254 megahertz spectrometer. Unless stated otherwise, gas chromatography was carried out on a 3 m 20% SE-52 column; conditions were as follows: 50°-250° C., 1.5 minute post injection interval, 25 degrees/minute.

EXAMPLE 1

Electrochemical Fluorination of 2-Thiophenecarbonyl Chloride to Prepare $F_5S(CF_2)_4COF$ Fluorochemical Product The electrochemical fluorination, by the Simons process, of 2-thiophenecarbonyl chloride, in the presence of dimethyl disulfide conductivity additive (10 wt.% of the thiophenecarbonyl fluoride), was carried out in a 1500 cc Simons cell of the type described in U.S. Pat. No. 2,713,593. The cell ran at 20-30 amperes, 0.069 MPa and 35° C. Some of the resulting fluorochemical product was taken off through an overhead condensing system at −40° C. which collected most of the product and the HF. The overhead fluorochemical product was phase-split to remove HF and analyzed by GC/FTIR and GC-MS; the analytical results were consistent with structures I and II, shown below, as the primary acyclic and cyclic perfluorinated substances present in the fluorochemical product (which also contained $F_5SC_4F_9$ by product).

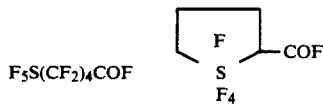

I      II

Cell drainings (789 g) derived from the above-described fluorination were treated with 73 g NaF to remove HF and filtered through a glass wool plug. A total of 641 g filtrate was obtained and 627 g of that material was fractionally distilled through a 3-plate Snyder distillation column with a splitter. Various fluorochemical product fractions were obtained from that distillation and similarly analyzed, each fraction comprising a mixture of substances with said structures I and II.

The Simons electrochemical fluorination of 2-thiophenecarbonyl fluoride, 2-thiophenecarboxylic acid, and 2-thiophenecarboxaldehyde were also carried out in a Simons cell to produce fluorochemical products, each comprising the corresponding acyclic and cyclic perfluorinated carbonyl fluorides, I and II.

EXAMPLE 2

Hydrolysis of $F_5S(CF_2)_4COF$ Fluorochemical Product to Prepare Carboxylic Acid Derivative Product Fifty grams of a distilled fraction (b.p. 95°-110° C.) of the cell drainings from thiophenecarbonyl chloride fluorination of Example 1 was added to 50 mL water with stirring. The stirring was stopped after 30 min. and the reaction mixture appeared to be a single phase. Concentrated $H_2SO_4$ (10 g) was added, and the mixture was stirred for 5 min., after which the mixture became two phases. The bottom fluorochemical phase was separated and washed with 20 mL concentrated $H_2SO_4$. A total of 43.6 g crude product was obtained. Distillation of this crude product at 0.1 torr pressure and a head temperature of 45°-47° C. gave 23.6 g purified product, the IR spectrum of which showed it to be a mixture of $F_5S(CF_2)_4CO_2H$ and the cyclic $SF_4C_4F_7CO_2H$. $F^{19}$ nmr spectroscopy showed the purified product to be 39 weight % $F_5S(CF_2)_4CO_2H$, 44 weight % cyclic $SF_4C_4F_7CO_2H$, and 17 weight unidentified sulfur-containing fluorochemical.

EXAMPLE 3

Preparation of $F_5S(CF_2)_4CO_2H$ Fluorochemical Product

Crude cell drainings derived electrochemical fluorination of 2-thiophenecarbonyl chloride by the Simons process were treated with NaF, filtered, and one-plate distilled. The material which distilled at a head temperature of 85° to 102° C. was retained and found to comprise a mixture of $F_5S(CF_2)_4COF$ and cyclic $SF_4C_4F_7COF$ by GC analysis. $LiOH \cdot H_2O$ (25.8 g) was dissolved in 105 g water and the distilled material (211 g) was added to the rapidly-stirred LiOH solution over a period of 10 min. The pH of the resulting solution approximately 7. Another 1.3 g LiOH $H_2O$ and 5 mL water was then added and the pH of the resulting solution was approximately 8. The solution was heated to 60° C. for 1.5 hrs. and then cooled to room temperature. Concentrated sulfuric acid (65 g) was added to the solution, and the resulting lower fluorochemical phase (187 g) was separated and distilled at aspirator pressure until the pot temperature reached 60° C. The remainder was distilled at 0.3 torr. A small precut was taken at a head temperature of 25°-53° C. (1.2 g). The remainder of the material distilled at a head temperature of 69°-75° C. (45.0 g); this material had a melting point of 20°-22° C. The refractive index of the distillate at 24° C. was 1.3248. A $F^{19}$ nmr spectrum of the distillate showed it to be a fluorochemical carboxylic acid product comprising principally (82.5 mole %) $F_5S(CF_2)_4CO_2H$ (in mole %) 0.8% cyclic $SF_4C_4F_7CO_2H$, 0.4% $CF_3SF_4(CF_2)_3CO_2H$, 6.4% $F_5SCF(CF_3)(CF_2)_2CO_2H$, 0.4% $F_5SCF(CF_3)CF_2CF_3$, 0.3% $F_5SCF(CF_3)CF(CF_3)_2$, 0.6% $F_5S(SF_2)_2CF(CF_3)CO_2$, 5.1% $F_5S(CF_2)_3CF_3$, 2.9% $F_5S(CF_2)_2CF(CF_3)_2$, and 0.6% $F_5S(CF_2)_2CF_2OCF_3$.

EXAMPLE 4

Preparation of $F_5S(CF_2)_4CO_2Li$ Product

Distilled fluorochemical carboxylic acid product (2.0 g) from Example 3, comprising predominantly $F_5S(CF_2H$, was placed in a crystallizing dish. $LiOH \cdot H_2O$ (0.23 g) was dissolved in 3 mL water and the solution was added dropwise with stirring to the acid product in the dish. The pH of the resulting solution was 6. The filled dish was placed in an oven at 80° C. overnight and then was dried at 100° C. for 1.5 hr. A total of 2.1 g of a white solid was recovered from the dish. The IR spectrum of the solid was consistent with that expected for the desired lithium salt, $F_5S(CF_2)_4CO_2Li$. Thermogravimetric analysis of the solid showed the following: onset of weight loss at 240° C., 50 weight percent loss at 292° C., and stabilized at 9.1 weight percent at 320° C. to 740° C.

EXAMPLE 5

Preparation of $F_5S(CF_2)_4CO_2NH_4$ Product

Distilled fluorochemical carboxylic acid product (2.0 g) from Example 3, comprising predominantly $F_5S(CF_2)_4CO_2H$, was placed in a crystallizing dish. Concentrated ammonium hydroxide (30%, 0.3 g) was dissolved in 2 mL water and the solution was added dropwise with stirring to the carboxylic acid product in the crystallizing dish. The pH of the resulting solution was 6. The filled dish was placed in an oven at 80° C. overnight and then was dried at 100° C. for 1.5 hr. A total of 1.75 g of a white solid was recovered from the dish. The IR spectrum of the solid was consistent with that expected for the desired ammonium salt, $F_5S(CF_2)_4CO_2NH_4$. The thermogravimetric analysis of the solid showed the following: onset of weight loss at 179° C., 50 weight percent loss at 203° C., and stabilized at zero weight percent remaining at 251° C. In comparison, the thermogravimetric analysis of $C_7F_{15}CO_2NH_4$ showed a similar weight loss profile but $F_5SCF_2CO_2Na$ showed an onset weight loss at 161° C. and stabilized at 12.5 weight percent at 175° C. up to 720° C.

EXAMPLE 6

Preparation of $F_5S(CF_2)_4CO_2CH_3$ Product

Forty nine g of a distilled fraction (b.p. 95°-110° C.) of the cell drainings from Example 1 was added to 48.6 g $BF_3 \cdot CH_3OH$ at 15 C. The reaction mixture was stirred at 23° C. for 30 min., and then 100 mL of water was added. The bottom fluorochemical phase was separated (48 g) and distilled at ambient pressure through a 3-plate Snyder column. GC-mass spectral analysis confirmed that each of the four fractions comprised predominantly $F_5S(CF_2)_4CO_2CH_3$ and cyclo- $F_4SC_4F_9CO_2CH_3$.

EXAMPLE 7

Preparation of $F_4S(CF_2)_4CH_2OH$ Product

Distilled product (115 g) of Example 3, comprising predominantly $F_5S(CF_2)_4CO_2H$, was dissolved in a mixture of 20 g methanol and 40 g concentrated sulfuric acid and the resulting solution was heated at 65°-70° C. for 9 hrs. The resulting crude product was cooled to room temperature, and the bottom fluorochemical phase was separated from the methanol/sulfuric acid phase. The fluorochemical phase was washed with 80 mL water; a total of 114.9 g of crude esterification product was obtained. The crude esterification product was treated with 5 g of silica gel, filtered, and was then distilled at ambient pressure. A small precut distilled at a head temperature of 110°–135° C. (9.4 g). The main cut distilled at a head temperature of 135°–166° C. (88 g) and was then reduced as follows.

Sodium borohydride (4.7 g) was added to 100 g tetraglyme with rapid stirring. At room temperature the distilled main cut, 80 g, was added to the sodium borohydride solution over a period of 1.5 hrs. The crude reaction mixture was heated to 64° C. and held at that temperature for one hr. The reaction product then was cooled to room temperature, and 100 mL of water was added, followed by 6 g concentrated sulfuric acid. The reaction mixture was heated to 100° C., at which point an azeotrope of fluorochemical and water distilled out of the reaction mixture. Heating was continued until no more fluorochemical distilled out of the pot. The distillate was phase-split; a total of 71.8 g of a yellow foul-smelling liquid, was collected and found to contain 3 wt % water. The liquid was added to 11 g polyphosphoric acid and distilled through a 3-plate Snyder column (bubble-pack) at 130 torr. The GC-mass spectral and $F^{19}$ nmr analyses showed each of the various distillate cuts to be a fluorochemical alcohol product comprising predominantly $F_5S(CF_2)_4CH_2OH$.

EXAMPLE 8

Preparation of $F_5S(CF_2)_4CH_2OCOCH=CH_2$ Product

Trifluoroacetic anhydride (16.5 g) was weighed into a polyethylene bottle and cooled in an ice bath for 15 min. Acrylic acid (5.7 g) was slowly added to the polyethylene bottle with magnetic stirring. The contents of the bottle were stirred in an ice bath for 30 min. A sample (20 g) of the alcohol product from Example 8, comprising $F_5S(CF_2)_4CH_2OH$, was placed in a flask with a mechanical stirrer and was cooled to 10° C. The contents of the polyethylene bottle were then added to the flask and stirred at 10° C. for 30 min. The ice bath was removed and the reaction mixture was stirred with warming to room temperature over one hr. The crude reaction mixture was poured into 50 mL of water and the fluorochemical phase was separated; a total of 22.4 g fluorochemical was obtained. The crude fluorochemical product was distilled at a pressure of 2.0 torr after the addition of 0.01 g of phenathiazine to the pot. A precut distilled at a head temperature of 30°–37° C. and weighed 1.3 g. A fraction was distilled at a head temperature of 37°–42° C. and weighed 14.4 g. GC-mass spectral analysis and $F^{19}$ nmr analysis showed the distilled fraction to be a fluorochemical acrylate product comprising $F_5S(CF_2)_4CH_2OCOCH=CH_2$; it had a density of 1.775 g/mL and a refractive index of 1.3455 at 23° C.

EXAMPLE 9

Preparation of $F_5S(CF_2)_4CH_2OCOCH=CH_2$ Product

Five grams of the acrylate product from Example 8, $F_5S(CF_2)_4CH_2OCOCH=CH_2$, was dissolved in 45 g Freon TM 113 solvent with 0.05 g Vas TM 62 azobis(isobutyronitrile and the mixture was heated at 55° C. for 18 hrs. H-nmr analysis of the polymer solution showed it to comprise 72 mole % of the homopolymer of $F_5S(CF_2)_4CH_2OCOCH=CH_2$. At the end of that time, 11.5 g portion of the resulting solution was added to 33 g methanol, whereupon a sticky precipitate formed. The liquid was decanted off, and the precipitate was washed with an additional 20 g methanol. The precipitate was then transferred to a dish and dried overnight in a vacuum oven at 60° C. and 0.3 torr; a total of 0.53 g of sticky solid (the homopolymer) was obtained. Differential scanning calorimetry of the solid showed a $T_g$ of $-9.5°$ C.

EXAMPLE 10

Electrochemical Fluorination of Thiobutyrolactone

A Simons electrochemical cell of the type described in U.S. Pat. No. 2,713,593 with a current capacity of 15 amperes was charged with 750 g of anhydrous liquid hydrogen fluoride. Fifteen hundred g of thiobutyrolactone with dimethyl disulfide (5 wt % of the thiobutyrolactone) was charged periodically to the cell with additional make-up HF. The cell was operated continuously at 0 to 25 amperes, 5.5 to 7.0 volts, and 0.022 to 0.103 MPa pressure. The gaseous product mixture from the cell was condensed. The liquid fluorochemical product mixture in the condensate was phase-split to remove liquid HF; the lower phase was the liquid fluorochemical product. A total of 2400 g of crude fluorochemical product was isolated, comprising $F_5S(CF_2)_3COF$.

A 95 g amount of cell drainings (95 g) derived from a similar Simons electrochemical fluorination of thiobutyrolactone were treated with NaF, filtered through a glass wool plug and distilled. $F^{19}$ nmr analysis of a cut showed to it comprise $F_5S(CF_2)_3COF$.

EXAMPLE 11

Preparation of $F_5S(CF_2)_3CO_2CH_3$ Product

Seventeen grams of a carbonyl fluoride cut (b.p. 70°–79° C.) from Example 10 was added to 16 g $BF_3 \cdot CH_3OH$. The reaction mixture was vigorous agitated for 5 min, and then 50 mL water was added. The crude fluorochemical product was phase-split from the methanol/water phase; 15.2 g crude fluorochemical product was isolated. The crude product was distilled through a column of glass helices with a splitter at ambient pressure. Cut 1 distilled at a head temperature of 70°–110° C. and weighed 5.7 g. Cut 2 distilled at 110°–130° C. and weighed 4.8 g. Cut 3 distilled at 130°–136° C. and weighed 1.0 g. The 9 nmr spectrum of cut 3 showed the following mole % composition: 95.3% $F_5S(CF_2)_3CO_2CH_3$, 3.5% $F_5SCF(CF_3)CF_2CO_2CH_3$, and 1.2% $F_5SCF_2CF(CF_3)CO_2CH_3$.

EXAMPLE 12

Preparation of $F_5S(CF_2)_3CH_2OH$ Product

Sodium borohydride (0.32 g) was added to 25 g tetraglyme with rapid stirring. At room temperature 4.8 g of Cut 2 (b.p. 110°–130° C.) from Example 11, $F_5S(CF_2)_3CO_2CH_3$, was added to the sodium borohydride solution over a period of 1.5 hrs. The crude reaction mixture was heated to 47° C. and held at that temperature for one hr. The reaction mixture then was cooled to room temperature and 50 mL water was added. After the water was added, 1 mL of concentrated sulfuric acid was introduced. The reaction mixture was heated to 100° C., at which point an azeotrope of the fluorochemical and water distilled from the reaction mixture. The crude reaction mixture was heated until no more fluorochemical distillate was produced. The water and fluorochemical were phase-separated. A total of 2.2 g crude fluorochemical, a yellow foul-smelling liquid, was collected. GC-mass spectral, IR, and $F^{19}$ nmr spectral analyses showed the liquid to comprise following composition (in mole %): 90.9%

$F_5S(CF_2)_3CH_2OH$, 1.5% $F_5SCF(CF_3)CF_2CH_2OH$, 0.4% $F_5SCF_2CF(CF_3)CH_2OH$, 3.3% $F_5S(CF_2)_3CH(OH)_2$, 3.8% $F_5S(CF_2)_3CH(OH)(CH_3)$ or $F_5S(CF_2)_3CH(OH)(CH_2R_f)$.

EXAMPLE 13

Electrochemical Fluorination of Di-(Thiohexanoyl Chloride)

A 15-ampere cell of the type described in U.S. Pat. No. 2,713,593 was charged with 750 g of anhydrous liquid hydrogen fluoride. Di-(thiohexanoyl chloride), (682 g) with dimethyl disulfide (5 wt % of the chloride) was charged periodically to the cell with additional make-up HF. The cell was operated continuously at 10 to 12 amperes, 4.8 to 6.0 volts, and 1.75 Kg/cm² pressure. The gaseous product mixture from the cell was condensed at −40° C. The liquid fluorochemical product in the condensate was phase-split from the liquid HF; the lower phase was the liquid fluorochemical product. A total of 1186 g crude fluorochemical product was isolated.

A portion (673 g) of the crude cell drainings were treated with 28 g NaF, filtered, and distilled through a 6-plate Snyder column with a reflux splitter. Three samples of different fluorochemical cuts were analyzed by treatment with methanol and subjected to GC analysis. One of the samples (derived from a cut with a b.p. of 101°–108° C.) was found to contain $F_5S(CF_2)_3CF(CF_3)COF$, $F_5SCF(CF_3)(CF)_3COF$, and $F_5S(CF_2)_5COF$. Another sample (derived from a cut with a b.p. of 108°–127° C.) was found to contain $F_5S(CF_2)_3CF(CF_3)COF$, $F_5SCF(CF_3)(CF_2)_3COF$, and $F_5S(CF_2)_5COF$. The third sample (derived from a cut with a b.p. of 127°–158° C.) was found to contain $F_5S(CF_2)_3CF(CF_3)COF$, $F_5SCF(CF_3)(CF_2)_3COF$, and $F_5S(CF_2)_5COF$.

EXAMPLE 14

Preparation of $F_5S(CF_2)_5CO_2H$ Product

LiOH H₂O (4.6 g) was dissolved in 20 g water. Distilled cell drainings (56 g) from Example 13 (two cuts with boiling points of 108°–127° C. and 127°–158° C.) were added to the rapidly-stirred LiOH solution over a period of 10 min. The pH of the resulting solution was approximately 8. The solution was heated to 60° C. for 1.5 hrs and then cooled to room temperature. Concentrated sulfuric acid (5.5 g) was added to the reaction mixture and the lower fluorochemical phase (51.4 g) was phase-separated. The fluorochemical phase was heated at aspirator pressure until the pot temperature reached 60° C. (18.2 g remaining). The de-aired carboxylic acid was then distilled at 0.3 torr pressure at a head temperature of 65°–69° C. (5.8 g). The F¹⁹ nmr spectrum of the distilled carboxylic acid product showed the following distribution of components (mole %): 2.0% $CF_3SF_4(CF_2)_4CO_2H$, 11.2% $F_5SCF(CF_3)(CF_2)_3CO_2H$, 4.9% $F_5SCF(CF_3)CF_2CF_2CF_3$, 56.1% $F_5S(CF_2)_5$, 5% $F_5S(CF_2)_3CF(CF_3)CO_2H$, 12.9% $F_5S(CF_2)_4CF_3$, 1.1% $F_5S(CF_2)_3CF(CF_3)_2$, 0.4% $F_5S(CF_2)_3CF_2OCF_3$.

EXAMPLE 15

Preparation of $SF_5(CF_2)_5CO_2NH_4$ Product

Distilled carboxylic acid product from Example 14, $F_5S(CF_2)_5CO_2H$ (1.17 g), was placed in a crystallizing dish. Concentrated ammonium hydroxide (30%, 0.2 g) was dissolved in 2 mL water and added dropwise to the dish with stirring. The pH was then 6. The dish was placed in an oven at 80° C. overnight and then dried at 100° C. for 1.5 hr. A total of 1.05 g of a white solid was recovered from the dish. The IR spectrum of the solid was consistent with the desired ammonium salt, $F_5S(CF_2)CO_2NH_4$.

EXAMPLE 16

Surface Energy of Fluorochemical Acrylate Polymer Films

Freon TM 113 solvent (20.9 g was mixed with 13.9 g of an 11 wt % solution of the acrylate homopolymer of Example 9. A clean microscope slide was dipped in the solution for one min. and then dried under vacuum at 0.3 torr and 60° C. for 3 hrs. At the end of this period, the slide was cooled to room temperature, and the contact angles of the resulting film or coating with Nujol mineral oil and glycerol were measured. The contact angle for Nujol mineral oil was 75° (average over three trials), and for glycerol was 119° (average over three trials). Similar runs with poly(1,1-dihydroperfluorooctyl methacrylate) gave contact angles of 82° for Nujol mineral oil and 117° for glycerol.

Using an IBM computer program (based on the Fowles derivation of Young's equation) for calculation of surface energies of films based on their contact angles with Nujol mineral oil and glycerol, the surface energy of the poly-$F_5S(CF_2)_4CH_2OCOCH=CH_2$ film was found to be 13.1 dynes/cm and the surface energy of poly—$CF_3(CF_2)_6CH_2OCOC(CH_3)=CH_2$ was found to be 10.7 dynes/cm.

EXAMPLE 17

Surface Tension of Aqueous Solutions Containing Fluorochemicals

The surface tension of the fluorochemical salt products from Examples 4, 5, and 15 was measured in water using a DuNuoy ring tensiometer. The results at various concentrations were compared with those for comparable $CF_3$-terminated fluorochemicals obtained commercially. The results appear in the table below.

| | Surface tension, (dynes/cm) | | | | | |
|---|---|---|---|---|---|---|
| | Concentration (ppm) of fluorochemical in aqueous Solution | | | | | |
| Fluorochemical | 20 | 50 | 100 | 500 | 1000 | 5000 |
| $F_5S(CF_2)_4CO_2Li$ | 71.4 | 70.3 | 68.4 | 61.1 | 57.3 | 38.4 |
| $F_5S(CF_2)_4CO_2NH_4$ | 71.0 | 70.2 | 68.9 | 60.7 | 54.7 | 33.1 |
| $CF_3(CF_2)_4CO_2Li$ | 71.4 | 70.8 | 70.6 | 69.3 | 67.6 | 57.8 |
| $F_5S(CF_2)_5CO_2NH_4$ | 68.3 | 63.3 | 58.2 | 41.1 | 31.9 | 22.0 |
| $CF_3(CF_2)_6CO_2NH_4$ | — | 68.1 | 65.0 | 54.7 | 46.1 | 29.6 |

The above data show that $F_5S$-terminated carboxylates of this invention are more effective surface active agents, i.e., lower surface tensions are achieved, than with the $CF_3$-terminated fluorochemical analog having a comparable number of carbon atoms.

EXAMPLE 18

Electrochemical Fluorination of 2-Mercaptobenzoic Acid to 2-($F_5S$)-cyclo-$C_6F_{10}COF$ A 25-ampere cell of the type described in U.S. Pat. No. 2,713,593 was charged with 1500 g anhydrous liquid HF. Since the organic starting material was found to be only slightly soluble in HF, a solids charger with the 2-mercaptobenzoic acid and dimethyl disulfide was installed in the returning HF line between the condenser and the fluorination cell body. By means of this system, 373 g 2-mercaptobenzoic acid along with 93 g dimethyl disulfide was fed to the cell over a period of 198 hrs along with make-up HF. The cell was operated continuously at 6.25 volts, 5 to 20 amperes, 35° C., and 0.105 mPa. The gaseous product mixture from the cell was condensed and the liquid fluorochemical product mixture from the cell was condensed snd the liquid fluorochemical product mixture, present as a lower layer, was separated from the HF layer to yield 757 g crude fluorochemical product. GC-mass spectrum of crude cell drainings which had been trated with methanol confirmed the presence of 2-($F_5S$)-cyclo-$C_6F_{10}CO_2CH_3$, 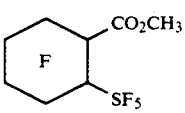

EXAMPLE 19

Preparation of 2($F_5S$)-cyclo-$C_6F_{10}CO_2CH_3$

Crude cell drainings as described in Example 19 (500 g) was cautiously added to 210 g methanol in a plastic bottle. The bottle was shaken for 2 min and allowed to cool to room temperature. At this time 210 g water was added and the phases were allowed to separate. A total of 492 g crude fluorochemical product was isolated. The material was distilled at ambient pressure. GC analysis of a cut (143°-170° C.) revealed that it contained cis and trans isomers of the desired product at 19.5% and 6.0%. GC-mass spectrum confirmed these peaks as isomeric ($F_5S$)—cyclo—$C_6F_{10}CO_2CH_3$.

EXAMPLE 20

Electrochemical Fluorination of 3-Methyl-2-Thiophenecarboxylic Acid

3-Methyl-2-thiophenecarboxylic acid was dissolved in anhydrous HF to form a 50 weight % solution. Ten weight % dimethyl disulfide (based on the weight of the thiophenecarboxylic acid), was added and the bottle agitated. The resultant solution, as taught in U.S. Pat. No. 3,028,321, was fed to the system and electrochemically fluorinated at 20° C. as described in U.S. Pat. No. 4,788,339 in Examples 40-44. GC mass spectrum of the crude fluorinated product showed it to contain 1.5 area % of the ring-opened $SF_5(CF_2)_2CF(CF_3)CF_2COF$ and none of the ring-intact $SF_4$- compound.

EXAMPLE 21

Electrochemical Fluorination of 5-Methyl-2-Thiophenecarboxylic Acid

5-Methyl-2-thiophenecarboxylic acid was dissolved in anhydrous HF to form a 50 weight % solution. Ten weight % dimethyl disulfide (based on the weight of the thiophenecarboxylic acid) was added and the bottle agitated. The resultant solution, as described in Example 32, was fed into the Simons electrochemical fluorination cell. GC-mass spectrum of the crude fluorinated product showed it to contain $F_5SCF(CF_3)(CF_2)_3COF$ and none of the ring-intact $SF_4$- compound.

EXAMPLE 22

Preparation of $F_5S(CF_2)_3CO_2CH_2(CF_2)_3CH_2OCO(CF_2)_3SF_5$

The diol, $HOCH_2(CF_2)_3CH_2OH$, (15.3 g), was dissolved in 14.7 g of triethylamine and 50 g of tetrahydrofuran. With good stirring, distilled $F_5S(CF_2)_3COF$ (148 g, 32% acid fluoride) was added to the flask over a 30-min. period. During the addition, the internal temperature rose to 32° C. Stirring was continued for an additional hour at room temperature. The tetrahydrofuran was then stripped off at aspirator pressure until the pot reached 40° C. Freon TM 113 solvent (100 mL) was added and the batch allowed to split. The bottom fluorochemical layer was washed two times with 100 mL of water. The fluorochemical phase was dried with 20 g of silica gel and filtered. The Freon TM 113 solvent was then stripped off on the rotary evaporator to give 39.2 g of product. The stripped product was dried by applying 1 torr vacuum for one hr; a total of 27.7 g crude product was isolated. H-nmr showed this material to contain 82 mole % $F_5S(CF_2)_3CO_2CH_2(CF_2)_3SF_5$, and 18% $HOCH_2(CF_2)_3CH_2OCO(CF_2)_3SF_5$.

EXAMPLE 23

Electrochemical Fluorination of 2-Thiophenesulfonylfluoride to Produce $F_5S(CF_2)_4SO_2F$ Product A 25-ampere cell of the type described in U.S. Pat. No. 2,713,593 was charged with 1500 g anhydrous liquid HF. A mixture of 710 g 2-thiophenesulfonyl fluoride and 71 g dimethyl disulfide was charged periodically to the cell with additional hydrogen fluoride as make-up. The cell was operated continuously at 6.2 volts, 23 amperes, 45° C., and 0.138 MPa. The gaseous product mixture from the cell was condensed and the liquid fluorochemical product mixture, present as lower layer, was separated from the HF layer to yield 779 g crude fluorochemical product. GC analysis showed the crude product to comprise $CF_3(CF_2)_3SO_2F$, cyclo—$C_4F_7$—$SF_4$—$SO_2F$, and $F_5S(CF_2)_4SO_2F$. GC-mass spectrum of the crude product confirmed these structural assignments.

The crude cell drainings (779 g) were washed with 800 mL water, dried with 50 g silica gel, and filtered to give 772 g. A portion (513 g) of the crude product was fractionally distilled through a six plate column with a reflux splitter. GC analysis showed the cuts to comprise mixtures of cyclic—$C_4F_7$—$SF_4$—$SO_2F$ and $F_5S(CF_2)_4SO_2F$.

EXAMPLE 24

Preparation of $F_5S(CF_2)_4SO_3Li$

A 10-gram mixture of $F_5S(CF_2)_4SO_2F$ (47.5 wt %) and cyclo—$SF_4C_4F_7SO_2F$ (52 wt %) was charged to a flask containing LiOH $H_2O$ (2.3 g) slurried in 30 g methanol. The reaction mixture was refluxed 18 hrs and then cooled to room temperature. The LiF was then filtered away. The cake was washed with an additional 30 mL methanol. The filtrate was placed in a dish and placed in an oven at 80° C. overnight. A total of 5.5 g of lithium salt, an off-white solid, was removed from the dish. IR analysis of the solid was consistant for the desired lithium salt: $F_5S(CF_2)_4SO_3Li$.

EXAMPLE 25

Preparation of $F_5S(CF_2)_4OCF(CF_3)COF$ From $F_5S(CF_2)_3COF$

A 500 mL flask was fitted with a $-78°$ C. condenser, gas addition line, and overhead stirrer under positive pressure of dry nitrogen. Into this flask was added 2.2 g KI, 75 g tetraethylene glycol dimethyl ether (tetraglyme), and 100 g fluorochemical product of Example 10 containing 34% $F_5S(CF_2)_3COF$. The resulting mixture was stirred at room temperature for one hr before cooling to $-22°$ C. and then addition of hexafluoropropylene oxide to it was begun via a gas addition line. Over a period of 1.5 hrs, 46 g of hexafluoropropylene was added. The reaction mixture was allowed to stand warm at room temperature overnight. The fluorochemical phase was split away from the black tetraglyme phase. A total of 130 g crude fluorochemical product was obtained. A small aliquot of the crude product was treated with methanol and analyzed by GC, which showed it to comprise $F_5S(CF_2)_4OCF(CF_3)COF$ and some unreacted $F_5(CF_2)COF$. The material was distilled through a three-plate bubble-pack (Snyder) column with a reflux splitter. The table below shows the cuts taken and amounts of desired fluorochemical.

| DISTILLATION OF CRUDE $F_5S(CF_2)_4OCF(CF_3)COF$ | | | |
|---|---|---|---|
| | Pot Temp °C. | Head Temp °C. | Weight g | Amount GC area |
| 1 | 60–80 | 110–120 | 48 | — |
| 2 | 80–104 | 120–126 | 14 | — |
| 3 | 104–122 | 126–146 | 26 | 22.9 |
| 4 | 122–130 | 146–156 | 21 | 72 |

F-nmr analysis of cut 4 showed it comprised 91.7 mole %
$F_5S(CF_2)_4OCF(CF_3)COF$, 5.6 mole % cyclo-$(C_4F_7O)$—$R_f$, 1.8%

F-nmr analysis of cut 4 showed it comprised 91.7 mole % $F_5S(CF_2)_4OCF(CF_3)COF$, 5.6 mole % cyclo-$(C_4F_7O)$—$R_f$, 1.8 % $F_5S$—$CF(CF_3)$—$R_f$, and 0.9 % $CF_3OR_f$, where $R_f$ is an inert fluorocarbon moiety.

Various modifications and variations of this invention will become apparent to those skilled in the art without departing from the scope and spirit of this invention.

What is claimed is:

1. Fluorochemical composition comprising one or a mixture of pentafluorosulfanyl, saturated fluoroaliphatic carbonyl or sulfonyl fluorides, wherein the fluoroaliphatic moiety in said acid fluorides comprises at least three fully-fluorinated carbon atoms.

2. The fluorochemical composition of claim 1 wherein said fluorides have the general formula $F_5S$—$R_f$—X where X is COF or $SO_2F$, and $R_f$ is a saturated fluoroaliphatic radical having a chain of at least three fully-fluorinated carbon atoms, one of which is bonded to the sulfur atom of the depicted $F_5S$ moiety in said formula.

3. The fluorochemical composition of claim 2 wherein said $R_f$ is —$C_nF_{2n}$— where n is at least 3.

4. The fluorochemical composition of claim 2 wherein said $R_f$ is a saturated perfluorocycloaliphatic moiety.

5. The fluorochemical composition of claim 2 wherein said $R_f$ is cyclohexylene.

6. The fluorochemical composition of claim 2 wherein $F_5S$—$R_f$—X is $F_5S$—$C_3F_6$—COF.

7. The fluorochemical composition of claim 2 wherein $F_5S$—$R_f$—X is $F_5S$—$C_4F_8$—COF.

8. The fluorochemical composition of claim 2 wherein $F_5S$—$R_f$—X is $F_5S$—$C_5F_{10}$—COF.

9. The fluorochemical composition of claim 2 wherein $F_5S$—$R_f$—X is

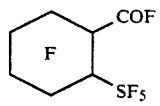

10. Fluorochemical composition comprising a derivative of a pentafluorosulfanyl, saturated fluoroaliphatic carbonyl or sulfonyl fluoride, said derivative having a fluoroaliphatic moiety comprising at least three fully-fluorinated carbon atoms.

11. Fluorochemical composition comprising a compound of the formula $F_5S$—$R_f$—Z where $R_f$ is a saturated fluoroaliphatic radical having a chain of at least three fully-fluorinated carbon atoms, one of which is bonded to the sulfur atom of the $F_5S$ moiety depicted in said formula, and Z is an organic moiety or an oxygen-containing inorganic moiety, wherein Z is a functional group capable of undergoing electrophilic, nucleophilic, or free radical reactions.

12. The fluorochemical composition of claim 11 wherein Z is —COOH or —$SO_3H$, or the ammonium, amine, or metal salt of either acid.

13. The fluorochemical composition of claim 11 herein Z contains a polymerizable group.

14. The fluorochemical composition of claim 10 wherein said derivative is $F_5S$—$C_3F_6$—COOH.

15. The fluorochemical composition of claim 10 wherein said derivative is $F_5S$—$C_4F_6$—COOH.

16. The fluorochemical composition of claim 10 wherein said derivative is $F_5S$—$C_5F_6$—COOH.

17. The fluorochemical composition of claim 10 wherein said derivative is $F_5S$—$C_4F_8$—COOLi.

18. The fluorochemical composition of claim 10 wherein said derivative is $F_5S$—$C_4F_8$—$COONH_4$.

19. The fluorochemical composition of claim 10 wherein said derivative is $F_5S$—$C_4F_8$—$COOCH_3$.

20. The fluorochemical composition of claim 10 wherein said derivative is $F_5S$—$C_4F_8$—$CH_2OH$.

21. The fluorochemical composition of claim 10 wherein said derivative is $F_5S$—$C_4F_8$—$CH_2OCOCH=CH_2$.

22. The fluorochemical composition of claim 10 wherein said derivative is $F_5S$—$C_3F_6$—$COOCH_3$.

23. The fluorochemical composition of claim 10 wherein said derivative is $F_5S$—$C_3F_6$—$CH_2OH$.

24. The fluorochemical composition of claim 10 wherein said derivative is $F_5S$—$C_3F_6$—$COOCH_2C_3F_6CH_2OCO$—$C_3F_6$—$SF_5$.

25. The fluorochemical composition of claim 10 wherein said derivative is $F_5S$—$C_5F_{10}$—$COONH_4$.

26. The fluorochemical composition of claim 10 wherein said derivative is

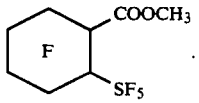

27. The fluorochemical composition of claim 10 wherein said $F_5S$—$R_4$—S is $F_5S$—$C_4F_8$—$SO_2F$.

UNITED STATES PATENT AND TRADEMARK OFFICE
CERTIFICATE OF CORRECTION

PATENT NO. : 5,159,105

DATED : October 27, 1992

INVENTOR(S) : Hansen et al.

It is certified that error appears in the above-identified patent and that said Letters Patent is hereby corrected as shown below:

```
Col. 3, line 10, Delete one -- . -- after "al"

Col. 3, line 19, Insert -- . -- after "Relat"

Col. 3, line 51, Replace "thermally" with --thermal--

Col. 5, line 2, Insert -- - -- after "-(CF2)8"

Col. 8, line 59, Replace "F4S" with --F5S--

Col. 8, line 60, Replace "N(C5H5)3" with --N(C2H5)3--

Col. 9, line 5, --2-- should be on the same line as "F5S-
                Rf....--

Col. 9, line 35, Replace "F4S" with --F5S--

Col. 9, line 53, Replace "F5SR4" with --F5SRf--

Col. 9, line 57, Replace "R4" with --Rf--

Col. 9, line 62, Delete --:-- after second "N"

Col. 10, line 30, Insert --)-- after "Stern"

Col. 13, line 42, Replace "LiOH.H2O" with --LiOH·H2O--

Col. 14, line 6, Replace "F5S(CF2H" with --F5S(CF2)4CO2H--

Col. 14, line 58, Replace the "4" after F with --5--
```

UNITED STATES PATENT AND TRADEMARK OFFICE
CERTIFICATE OF CORRECTION

PATENT NO. : 5,159,105

DATED : October 27, 1992

INVENTOR(S) : Hansen et al.

It is certified that error appears in the above-identified patent and that said Letters Patent is hereby corrected as shown below:

Col. 15, line 59, Insert --)-- after "isobutyronitrile"

Col. 16, line 27, Replace "to it" with --it to--

Col. 16, line 42, Replace "9" with --$F^{19}$--

Col. 17, line 29, Replace "$F_5SCF(CF_3)(CF)_3COF$" with --$F_5SCF(CF_3)(CF_2)_3COF$--

Col. 17, line 58, Replace "$F_5S(CF_2)$" with --$F_5S(CF_2)_5CO_2H$,--

Col. 18, line 11, Insert --)-- after "(20.9 g"

Col. 19, line 9, Replace "snd" with --and--

Col. 19, line 14, Replace "trated" with --treated--

Col. 19, line 25, Insert -- - -- between "2("

Col. 20, line 23, Replace "$F_5S(CF_2)_3CO_2CH_2(CF_2)_3SF_5$" with --$F_5S(CF_2)_3CO_2CH_2(CF_2)_3CH_2OCO(CF_2)_3SF_5$--

Col. 20, line 24, Replace "$HOCH_2(CF_2)_3CH_2{_0}CO(CF_2)_3SF_5$" with --$HOCH_2(CF_2)_3CH_2OCO(CF_2)_3SF_5$--

Col. 20, line 59, Insert -- • -- between "LiOH H2O"

Col. 21, line 60, Replace "$F_f$" with --$R_f$--

UNITED STATES PATENT AND TRADEMARK OFFICE
CERTIFICATE OF CORRECTION

PATENT NO. : 5,159,105

DATED : October 27, 1992

INVENTOR(S) : Hansen et al.

It is certified that error appears in the above-identified patent and that said Letters Patent is hereby corrected as shown below:

Col. 22, line 54, Replace "$F_6-COOCH_2C_3F_6CH_2 0CO-C_3F_6-SF_5$" with --$F_6-COOCH_2C_3F_6CH_2OCO-C_3F_6-SF_5$--

Col. 22, line 67, Replace "$R_4$" with --$R_f$--

Signed and Sealed this

Sixteenth Day of November, 1993

BRUCE LEHMAN

*Attest:*

*Attesting Officer*   *Commissioner of Patents and Trademarks*